United States Patent
Yamashita et al.

(10) Patent No.: US 7,247,640 B2
(45) Date of Patent: Jul. 24, 2007

(54) MEDICAMENT FOR TREATMENT OF BONE MARROW SUPPRESSION, FOR TREATMENT OF INFECTIOUS DISEASES AND FOR INCREASING THE NUMBER OF LEUKOCYTES

(75) Inventors: Takumi Yamashita, Tokyo (JP); Chihiro Nishimura, Chiba (JP); Tetsushi Saino, Saitama (JP); Yasuhiko Muraoka, Tokyo (JP); Tomio Takeuchi, Tokyo (JP)

(73) Assignees: Nippon Kayaku Kabushiki Kaisha, Tokyo (JP); Zaidan Hojin Biseibutsu Kagaku Kenkyu Kai, Tokyo (JP)

( * ) Notice: Subject to any disclaimer, the term of this patent is extended or adjusted under 35 U.S.C. 154(b) by 0 days.

(21) Appl. No.: 11/187,073

(22) Filed: Jul. 22, 2005

(65) Prior Publication Data

US 2005/0256090 A1 Nov. 17, 2005

Related U.S. Application Data

(63) Continuation of application No. 10/433,362, filed on Jun. 3, 2003, now abandoned.

(30) Foreign Application Priority Data

Jan. 16, 2001 (JP) .............................. 2001-008233

(51) Int. Cl.
*A61K 31/435* (2006.01)
*A61K 31/40* (2006.01)
*C07D 221/92* (2006.01)

(52) U.S. Cl. ........................ 514/277; 514/359; 546/21; 548/412

(58) Field of Classification Search ................. 546/21; 514/277, 359; 548/412
See application file for complete search history.

(56) References Cited

U.S. PATENT DOCUMENTS

| 4,935,493 A | 6/1990 | Bachovchin et al. ....... 530/331 |
| 6,214,340 B1 | 4/2001 | Takeuchi et al. ............ 424/117 |
| 6,579,989 B1 | 6/2003 | Takeuchi et al. ............ 548/412 |

FOREIGN PATENT DOCUMENTS

| CA | 2 372 068 | 11/2000 |
| EP | 1 043 328 | 10/2000 |
| JP | 1-40036 | 8/1989 |
| JP | 2000-327689 | 11/2000 |
| WO | 94/03055 | 2/1994 |
| WO | 99/25719 | 5/1999 |
| WO | 99/56753 | 11/1999 |
| WO | 99/62914 | 12/1999 |
| WO | 00/69868 | 11/2000 |
| WO | WO00/69868 | * 11/2000 |

OTHER PUBLICATIONS

Tetsuo Akiyama et al Sep. 2001, Sulphostin, a Potent Inhibitor for Dipeptidyl Peptidase IV from Strptomyces sp. MK251-43F3.*
Caplus English abstract DN 143:90521 Abe Masatoshi et al 2005.*
Rami Komrokji et al, 2004, The colony-stimulating factors: use to prevent and treat neutropenia and its complications.*
Jared Adams et al, 2002, G-CSF as prophylaxis of febrile neutropenia in SCLC.*
Akiyama, Tetsuo et al., Sulphostin, a potent inhibitor for dipeptidyl peptidase IV from Streptomyces sp. MK251; -43F3, 2001, vol. 54, No. 9, pp. 744-746.
The International Search Report dated Apr. 16, 2002.

* cited by examiner

*Primary Examiner*—Rita Desai
(74) *Attorney, Agent, or Firm*—Nields & Lemack

(57) ABSTRACT

A medicament for prophylaxis or treatment of bone marrow suppression, for treatment of infectious diseases and for increasing the number of leukocytes, which comprise as an active ingredient a sulphostin-related compound represented by general formula (I):

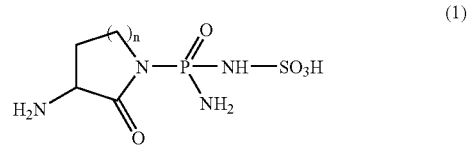

wherein n is an integer of 0 to 3, or a pharmacologically acceptable salt thereof.

5 Claims, 1 Drawing Sheet

* : SIGNIFICANT DIFFERENCE FROM CONTROL GROUP $p < 0.05$

MEDICAMENT FOR TREATMENT OF BONE MARROW SUPPRESSION, FOR TREATMENT OF INFECTIOUS DISEASES AND FOR INCREASING THE NUMBER OF LEUKOCYTES

This application is a Continuation of U.S. Ser. No. 10/433,362 filed Jun. 3, 2003 now abandoned, the disclosure of which is incorporated herein by reference.

TECHNICAL FIELD

The present invention relates to a medicament for prophylaxis or treatment of bone marrow suppression, for treatment of infectious diseases and for increasing the number of leukocytes, which contain a sulphostin-related compound or a pharmacologically acceptable salt thereof as an active ingredient.

BACKGROUND ART

It is known that the suppression of the functions of bone marrow by various causes seriously worsens systemic conditions to pose peril to life. As morbidities due to such bone marrow suppression symptoms, hypoplastic anemia, thrombo-cytopenia, leukopenia and the like are known.

The mechanisms of the onset of leukopenia among them are classified into those involving a decrease in leukocyte production and those involving the acceleration of leukocyte destruction. Causes for the decrease in leukocyte production include congenital diseases, irradiation with radiation, hypoplastic anemia, administration of an antitumor agent or antibiotic, etc. On the other hand, causes for the acceleration of leukocyte destruction include infectious diseases, immunological abnormalities, etc.

As a therapeutic method for leukopenia, the administration of granulocyte colony-stimulating factor (G-CSF) or macrophage-colony stimulating factor is a promising means at present. On the other hand, erythropoietin is used for treating erythropenia. The application of interleukin-6, interleukin-11, thrombopoietin and the like as medicine is in progress for treating thrombocytopenia. In addition, the application of interleukin-3, granulocyte-macrophage-colony stimulating factor (GM-CSF) and the like as therapeutic agent for bone marrow suppression is in progress.

On the other hand, for example, compounds formed by the substitution of an N-acyl-N-alkylamino group at the 1-position of a sugar are known (JP-B-1-40036) as compounds having defensive effect on infectious diseases caused by bacteria, fungi, etc.

Sulphostin can be obtained by culturing a microorganism belonging to the genus *Streptomyces* and compounds analogous thereto can be obtained by chemical synthesis. Sulphostin and the analogous compounds thereto are hereinafter referred to as sulphostin-related compounds. These sulphostin-related compounds have an inhibitory effect on dipeptidyl peptidase IV and hence are expected as physiologically active substances such as, for example, an immunomodulator, a hormone modulator, an anti-HIV agent, an antiallergic agent, an anti-inflammatory agent and an antirheumatic agent WO 99/25719 and JP-A-2000-327689).

DISCLOSURE OF THE INVENTION

The present invention is intended to provide a novel medicament for prophylaxis or treatment of bone marrow suppression, for treatment of infectious diseases and for increasing the number of leukocytes.

The present inventors earnestly investigated using a bone marrow suppression model induced by an anticancer agent. Consequently, the present inventors confirmed the leucopenia-curing effect of sulphostin-related compounds represented by general formula (I), and found that these compounds can be used as a medicament for prophylaxis or treatment of bone marrow suppression. In addition, the present inventors confirmed that the aforesaid sulphostin-related compounds are effective in increasing the number of leukocytes in a normal mouse. They found that these compounds can be used as a medicament for increasing the number of leukocytes and also that the compounds can be used as an active ingredient of a medicament for treatment of infectious diseases. The above references (WO 99/25719 and JP-A-2000-327689) referring to the sulphostin-related compounds neither disclose nor suggest that these compounds have therapeutic effect on bone marrow suppression and infectious diseases. The present inventors found for the first time the usefulness of these compounds as a medicament for treatment of bone marrow suppression, for treatment of infectious diseases and for increasing the number of leukocytes.

That is, the present invention relates to the following items (1) to (9).

(1) A medicament for prophilaxis or treatment of bone marrow suppression comprising as an active ingredient a sulphostin-related compound represented by general formula (I):

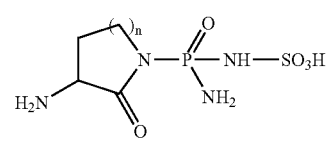

(1)

wherein n is an integer of 0 to 3, or a pharmacologically acceptable salt thereof.

(2) A medicament according to the above item 1, wherein n is an integer of 1 to 3 in general formula (I).

(3) A medicament according to the above item 1 or 2, wherein the bone marrow suppression is leukopenia.

(4) A medicament for treatment of infectious diseases comprising as an active ingredient a sulphostin-related compound represented by general formula (I):

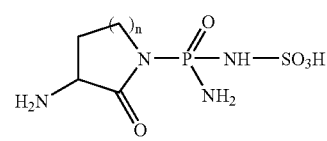

(1)

wherein n is an integer of 0 to 3, or a pharmacologically acceptable salt thereof.

(5) A medicament according to the above item 4, wherein n is an integer of 1 to 3 in general formula (I).

(6) A medicament for increasing the number of leukocytes comprising as an active ingredient a sulphostin-related compound represented by general formula (I):

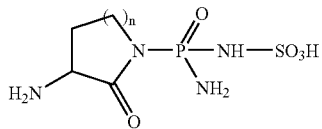

wherein n is an integer of 0 to 3, or a pharmacologically acceptable salt thereof.

(7) A medicament for increasing the number of leukocytes according to the above item 6, wherein n is an integer of 1 to 3 in general formula (I).

(8) Use of a sulphostin-related compound represented by general formula (I):

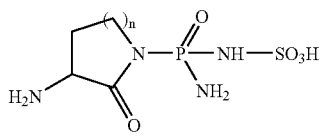

wherein n is an integer of 0 to 3, or a pharmacologically acceptable salt thereof, for producing a medicament for prophylaxis or treatment of bone marrow suppression, for treatment of infectious diseases or for increasing the number of leukocytes.

(9) A method for prophylaxis or treatment of bone marrow suppression, for treatment of infectious diseases or for increasing the number of leukocytes, which comprises administering a sulphostin-related compound represented by general formula (I):

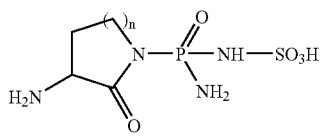

wherein n is an integer of 0 to 3, or a pharmacologically acceptable salt thereof, in a therapeutically effective amount.

BEST MODE FOR CARRYING OUT THE INVENTION

Figure 1:
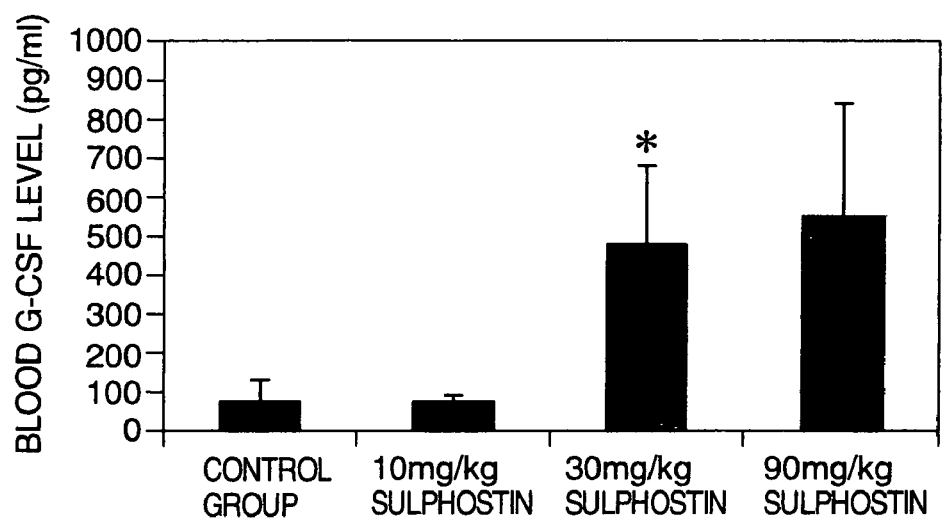
FIG. 1 shows an increase in blood G-CSF level caused by sulphostin.

The term "medicament for prophylaxis or treatment of bone marrow suppression" used herein means a medicament that can treat leukopenia, erythropenia and thrombocytopenia by inducing the production of blood cells such as leukocytes, erythrocytes and thrombocytes in the body when administered to a human being or an animal. Such a medicament is for prophylaxis or treatment of, for example, bone marrow suppression caused by radiotherapy, bone marrow transplantation, chemotherapy to cancer, an antibiotic or the like; and anemias such as renal anemia, hemorrhagic anemia, hemolytic anemia, deficiency anemia and the like. Such a medicament can be also used in the case of hypoplastic anemia, thrombocytopenia, leukopenia caused by an infectious disease, a viral disease, trophopathy or the like, exanthema thrombocytopenic purpura and the like. According to the present invention, the medicament is preferably used in the case of leukopenia.

The term "medicament for increasing the number of leukocytes" used herein means a medicament having a property of increasing the production of leukocytes in the body. Such a medicament can be used for prophylaxis and treatment of various diseases due to a decrease in leukocyte production caused by a congenital disease, irradiation with radiation, hypoplastic anemia, an antitumor agent, an antibiotic or the like, and various diseases due to the acceleration of leukocyte destruction by an infectious disease, an immunological abnormality or the like. Specifically, the medicament for increasing the number of leukocytes can be used, for example, for prophylaxis and treatment of a decrease in the number of leukocytes in the blood or a medicament for treating an infectious disease by increasing the number of leukocytes in the blood than normal conditions. The term "medicament for treatment of infectious diseases" means a medicament capable of increasing the production of leukocytes in the body to heighten defensive effect on, for example, bacterial or fungous infection or exert its therapeutic effect. The leukocytes include, for example, neutrophil, eosinophil, basophil, monocyte and lymphocyte.

The sulphostin-related compound of general formula (I) used in the present invention can be produced by the production process disclosed in WO 99/25719 or JP-A-2000-327689.

In the compound of general formula (I), n is an integer of 0 to 3, preferably 1 to 3. The compound of general formula (I) has optically active sites (chiral centers) at the ring-constituting carbon atom (C) at the joint of the amino group and at the phosphorus atom (P). The compound according to the present invention also includes optical isomers and racemic modifications due to each of the optically active sites.

Specific examples of the compound of general formula (1) are as follows:

3(S)-amino-1-((S)-amino(sulfoamino)-phosphinyl)-2-piperidone

3(S)-amino-1-((R)-amino(sulfoamino)-phosphinyl)-2-piperidone (, which is named sulphostin), 3(R)-amino-1-((R)-amino(sulfoamino)-phosphinyl)-2-piperidone, 3(R)-amino-1-((S)-amino(sulfoamino)-phosphinyl)-2-piperidone, 3(S)-amino-1-((R)-amino(sulfoamino)-phosphinyl)-2-caprolactam, 3(S)-amino-1-((S)-amino(sulfoamino)-phosphinyl)-2-caprolactam, 3(S)-amino-1-((S)-amino(sulfoamino)-phosphinyl)-2-pyrrolidone, and 3(S)-amino-1-((R)-amino(sulfoamino)-phosphinyl)-2-pyrrolidone.

According to the present invention, the compound of general formula (I) may be administered in the form of a pharmacologically acceptable salt when used in a medicament for prophylaxis or treatment of bone marrow suppression, for treatment of infectious diseases or for increasing the number of leukocytes. The salt includes, for example, salts with inorganic acids such as hydrochloric acid, sulfuric acid, phosphoric acid and the like; salts with organic acids such as p-toluenesulfonic acid and the like; salts with inorganic metals such as Na, K, Ca and the like; and salts with organic amines such as methylamine, ethylamine, diethanolamine and the like.

When the above-mentioned sulphostin-related compound or pharmacologically acceptable salt thereof of the present invention is used in the medicament for prophylaxis or treatment of bone marrow suppression, for treatment of infectious diseases or for increasing the number of leukocytes, various conventional methods can be adopted for the formulation and administration of said compound or salt thereof. As a method for the administration, injection, oral administration, rectal administration and the like are possible. As the pharmaceutical form of said compound or salt thereof, forms such as an injection, powder, granules, tablets, suppository and the like may be employed.

In the formulation, various pharmaceutical adjuvants, namely, carriers and other auxiliaries such as a stabilizer, antiseptic, soothing agent, emulsifier, etc. may be used if necessary so long as they have no undesirable influence on the sulphostin-related compound. The content of the sulphostin-related compound or pharmacologically acceptable salt thereof in the pharmaceutical preparation obtained by the formulation can be varied in a wide range, depending on the pharmaceutical form and the like. In general, the pharmaceutical preparation contains 0.01 to 100 wt %, preferably 0.1 to 70 wt %, of sulphostin or a salt thereof and the balance of a conventional pharmaceutical carrier and other adjuvants.

Although varied depending on symptoms, the dose of the sulphostin-related compound or pharmacologically acceptable salt thereof is approximately 0.01 to 800 mg a day for adult. When repetitive administration is necessary, the dose per day is preferably low.

The sulphostin-related compound as the medicament for prophylaxis or treatment of bone marrow suppression or for increasing the number of leukocytes of the present invention can be preventively administered to a patient who is expected to suffer from bone marrow suppression or the like. It is well known that the functions of bone marrow are very frequently suppressed, for example, when various diseases are treated by employing radiotherapy, an antitumor agent or an antibiotic. When such a patient who is expected to suffer from the suppression of functions of the bone marrow is cured with the sulphostin-related compound, it can be allowed to exert its prophylactic effect by its pre-administration or administration at the time of treatment.

Pharmacological experiment examples and formulation examples according to the present invention are described below as working examples, but they are not intended in any way to limit the scope of the present invention.

EXPERIMENT EXAMPLE 1

Test for Evaluating an Efficacy on Drug-Induced Leukopenia

Experimental Method and Results

The effect of sulphostin [3(S)-amino-1-((R)-amino(sulfoamino)phosphinyl)-2-piperidone] on drug-induced leukopenia was evaluated according to the method of Okabe et al. (Yakuri to Chiryo (Japanese Pharmacology and Therapeutics) Vol. 19, No. 6, p. 55, 1991).

ICR strain male mice (Crj:CD-1) aged 8 weeks were used in the test. The animals were divided into three groups of 3 or 4 animals per group.

On Day 0, cyclophosphamide was intraperitoneally administered once to all the groups in a dose of 200 mg/kg. From the next day, the following were intravenously and repeatedly administered to the groups, respectively, for 5 days (Day 1 to 5); the first group (a control group): physiological saline, the second group: sulphostin (30 mg/kg/day), and the third group: sulphostin (100 mg/kg/day). Blood was drawn from the posterior-eyehole venous plexus on Day 0 (before the administration of cyclophosphamide) and Days 2, 4, 6 and 8 (the blood drawing, however, was carried out only on Days 0, 4 and 6 in the case of the second group), and the number of leukocytes was periodically measured to investigate the leukocyte-increasing effect of sulphostin relative to a decrease of leukocytes caused by cyclophosphamide.

The results are shown in Table 1.

TABLE 1

Restoration of the number of leukocytes by sulphostin
(unit: ×100/millimeter cube)

| Group/Day | Control (n = 4) | Sulphostin 30 mg/kg (n = 3) | Sulphostin 100 mg/kg (n = 4) |
|---|---|---|---|
| Day 0 | 46 ± 12.4 (100%) | 44 ± 7.1 (100%) | 38 ± 17.2 (100%) |
| Day 2 | 12 ± 0.8 (26%) | ND | 21 ± 5.1 (55%) |
| Day 4 | 12 ± 1.3 (26%) | 13 ± 12.5 (30%) | 10 ± 6.3 (26%) |
| Day 6 | 22 ± 6.7 (48%) | 42 ± 14.5 (95%) | 48 ± 23.8 (126%) |
| Day 8 | 71 ± 27.7 (154%) | ND | 254 ± 75.5 (668%) |

The data are expressed as the mean±S.D and percentages based on the number of leukocytes on Day 0. ND refers to no data.

That is, the numbers of leukocytes of the control group were 100, 26, 26, 48 and 154% on Days 0, 2, 4, 6 and 8, respectively; the numbers of leukocytes of the sulphostin (30 mg/kg/day)-treated group were 100, 30 and 95% on Days 0, 4 and 6, respectively; and the numbers of leukocytes of the sulphostin (100 mg/kg/day)-treated group were 100, 55, 26, 126 and 668% on Days 0, 2, 4, 6 and 8, respectively. This fact reveals that the restoration of the number of leukocytes to the initial value after the administration of cyclophosphamide requires 8 days in the case of the control group and that the restoration requires only 6 days, namely, the restoration is faster, in the case of the sulphostin-treated groups. In addition, the data on Day 8 reveals that sulphostin is very effective in increasing the number of leukocytes.

EXPERIMENT EXAMPLE 2

Test for Investigating the Increase of Leukocytes in Normal Mice

Experimental Method

ICR strain male mice (Crj:CD-1) aged 7 weeks were used in the test. The animals were divided into 5 groups of 4 animals per group. The following were intravenously and repeatedly administered to the groups, respectively, for 5 days; the first group: physiological saline as solvent, the second group: sulphostin (2 mg/kg/day), the third group: sulphostin (10 mg/kg/day), the fourth group: sulphostin (50 mg/kg/day), and the fifth group: sulphostin (250 mg/kg/day). On the day subsequent to the last day of the administration period, blood was drawn from the abdominal aorta under anesthesia and the number of leukocytes was measured.

Results

Sulphostin increased the number of leukocytes to such an extent that the numbers of leukocytes of the sulphostin-treated groups were larger than that of the control group by the following factors; the sulphostin (2 mg/kg/day)-treated group: 1.4, the sulphostin (10 mg/kg/day)-treated group: 1.9, the sulphostin (50 mg/kg/day)-treated group: 4.9, and the sulphostin (250 mg/kg/day)-treated group: 5.9. Thus, it is revealed that sulphostin was very effective in increasing the number of leukocytes and hence useful as a medicament for prophylaxis or treatment of bone marrow suppression, infectious diseases and the like.

EXPERIMENT EXAMPLE 3

Test for Investigating the Increase of G-CSF Concentration in Normal Mice

ICR strain male mice (Crj:CD-1) aged 7 weeks were used in the test. The animals were divided into 4 groups of 5 animals per group. The following were intravenously and repeatedly administered to the groups, respectively, for 5 days; the first group: physiological saline as solvent, the second group: sulphostin (10 mg/kg/day), the third group: sulphostin (30 mg/kg/day), and the fourth group: sulphostin (90 mg/kg/day). On the day subsequent to completion of the administration, blood was drawn from the abdominal aorta under anesthesia. The blood obtained was centrifuged to collect plasma, and G-CSF was measured by the use of a mouse G-CSF ELISA measuring kit (R & D SYSTEMS Inc.).

The results are shown in FIG. 1.

Sulphostin increased G-CSF to such an extent that the G-CSF levels of the sulphostin-treated groups were higher than that of the control group by the following factors; the sulphostin (10 mg/kg)-treated group: 1.03, the sulphostin (30 mg/kg)-treated group: 6.1, and the sulphostin (90 mg/kg)-treated group: 7.0. Thus, it was confirmed that the sulphostin exerted its effect of increasing the number of neutrophils, through its powerful G-CSF secretory action. It was revealed that sulphostin was useful as a medicament for prophylaxis or treatment of bone marrow suppression, infectious diseases and the like.

FORMULATION EXAMPLE 1

Sulphostin, the compound according to the present invention was dissolved in physiological saline containing 30% (w/v) polyethylene glycol 400 to prepare a 0.05% solution of said compound, and this solution was filter-sterilized to produce a pharmaceutical preparation for intravenous injection containing 15 mg of said compound per vial.

FORMULATION EXAMPLE 2

Tablets each weighing 300 g were obtained by mixing 30 parts by weight of sulphostin, 120 parts of crystalline lactose, 147 parts of crystalline cellulose and 3 parts of magnesium stearate in a V-type blender, and compressing the mixture into tablets.

INDUSTRIAL APPLICABILITY

According to the present invention, it is confirmed that the sulphostin-related compounds are effective in restoring and increasing the number of leucocytes in a living body. Furthermore, it turns out that they are useful as a medicament for prophylaxis or treatment of bone marrow suppression, for treatment of infectious diseases caused by bacteria, fungi and the like, and for increasing the number of leucocytes.

The invention claimed is:

1. A method for treatment of neutropenia in a patient in need thereof, which comprises administering a sulphostin-related compound represented by formula (I):

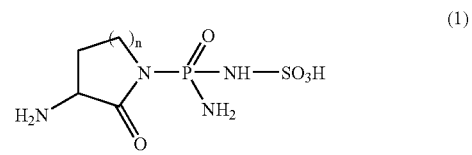

wherein n is an integer of 0 to 3, or a pharmacologically acceptable salt thereof, in a therapeutically effective amount.

2. A method according to claim 1, wherein n is an integer of 1 to 3 in formula (I).

3. A method for increasing the number of neutrophils in a patient in need thereof, which comprises administering a sulphostin-related compound represented by formula (I):

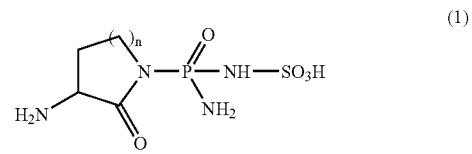

wherein n is an integer of 0 to 3, or a pharmacologically acceptable salt thereof, in a therapeutically effective amount.

4. A method for increasing the number of neutrophils according to claim 3, wherein n is an integer of 1 to 3 in formula (I).

5. A method for treatment of neutropenia, for increasing the number of leukocytes in a patient in need thereof, which comprises administering a sulphostin-related compound represented by formula (I):

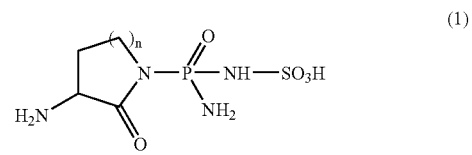

wherein n is an integer of 0 to 3, or a pharmacologically acceptable salt thereof, in a therapeutically effective amount.

* * * * *